United States Patent
Shiba et al.

(10) Patent No.: US 9,138,387 B2
(45) Date of Patent: Sep. 22, 2015

(54) ORAL COMPOSITION FOR REMOVING TOOTH STAIN

(71) Applicant: Regenetiss, Inc., Kawagishinishi, Okaya-shi Nagano (JP)

(72) Inventors: Toshikazu Shiba, Okaya (JP); Yumi Kawazoe, Okaya (JP); Shinichi Kato, Okaya (JP)

(73) Assignee: Regenetiss, Inc., Nagano (JP)

( * ) Notice: Subject to any disclaimer, the term of this patent is extended or adjusted under 35 U.S.C. 154(b) by 0 days.

(21) Appl. No.: 14/455,937

(22) Filed: Aug. 10, 2014

(65) Prior Publication Data

US 2014/0349253 A1    Nov. 27, 2014

Related U.S. Application Data

(62) Division of application No. 13/825,555, filed as application No. PCT/JP2011/071601 on Sep. 22, 2011, now abandoned.

(30) Foreign Application Priority Data

Sep. 23, 2010 (JP) ................................. 2010-212949

(51) Int. Cl.
| | |
|---|---|
| A61K 8/22 | (2006.01) |
| A61K 8/84 | (2006.01) |
| A61K 8/86 | (2006.01) |
| A61C 19/06 | (2006.01) |
| A61N 5/06 | (2006.01) |
| A61Q 11/00 | (2006.01) |
| A61K 8/24 | (2006.01) |
| A61K 8/42 | (2006.01) |

(52) U.S. Cl.
CPC ................. *A61K 8/22* (2013.01); *A61C 19/066* (2013.01); *A61K 8/24* (2013.01); *A61K 8/42* (2013.01); *A61K 8/84* (2013.01); *A61K 8/86* (2013.01); *A61N 5/062* (2013.01); *A61Q 11/00* (2013.01); *A61K 2800/75* (2013.01); *A61K 2800/81* (2013.01)

(58) Field of Classification Search
USPC ............................................ 424/53; 433/215
See application file for complete search history.

(56) References Cited

U.S. PATENT DOCUMENTS

| | | | |
|---|---|---|---|
| 3,337,466 A | 8/1967 | Puetzer et al. | |
| 4,661,070 A | 4/1987 | Friedman | |
| 2003/0082114 A1 | 5/2003 | Kim et al. | |
| 2006/0171907 A1* | 8/2006 | Scott et al. | ....................... 424/53 |
| 2007/0020584 A1* | 1/2007 | Madray | ........................ 433/215 |

FOREIGN PATENT DOCUMENTS

| | | |
|---|---|---|
| JP | 2002-284656 A | 10/2002 |
| JP | 2006-504776 | 2/2006 |
| JP | 2009-024009 | 2/2009 |
| JP | 2009-51734 | 3/2009 |
| JP | 2009-126819 | 6/2009 |
| KR | 10-2006-0116936 A | 11/2006 |
| WO | WO2007145287 A1 | 12/2007 |

OTHER PUBLICATIONS

Price et al., "The pH of Tooth-Whitening Products." J Can Dent Assoc 2000; 66:421-6.*
International Search Report of international patent application No. PCTJP2011/071601 completed on Dec. 7, 2011 and mailed Dec. 20, 2011 (2 pages).
Office Action of Korean application No. 10-2013-7010313 dated Sep. 29, 2014.

* cited by examiner

*Primary Examiner* — Walter Webb
(74) *Attorney, Agent, or Firm* — Pyprus Pte Ltd (57) ABSTRACT

The object of the present invention is to provide an oral composition, which can remove tooth stain effectively. The object of the present invention is also to provide an oral composition, which scarcely damages teeth and gums and can be easily applied. An oral composition for removing tooth stain, which comprises 3.5 to 30% by weight of peroxide and 5 to 20% by weight of phosphate polymer (in particular, ultraphosphate having an average chain length of phosphoric acid polymerization of 10 to 30).

11 Claims, 5 Drawing Sheets

Fig.1A

Before treatment    10 min    30 min

Fig.1B

Before treatment    10 min    30 min

Fig.2A
Before treatment    10 min    30 min

Fig.2B
Before treatment    10 min    30 min

Fig.3
Before treatment    10 min    30 min

Fig.4
Before treatment   3 min   10 min   30 min

ORAL COMPOSITION FOR REMOVING TOOTH STAIN

RELATED APPLICATIONS

This application is a divisional of application Ser. No. 13/825,555, filed Apr. 2, 2013, which is a National Stage of International Application No. PCT/JP2011/071601, filed Sep. 22, 2011, which claims the benefit of Japanese Application No. 2010-212949, filed Sep. 23, 2010, which are herein incorporated by references.

TECHNICAL FIELD

The present invention relates to an oral composition for removing tooth stain. In particular, the present invention relates to an oral composition which can remove tooth stain effectively by containing peroxides and phosphate polymers at a predetermined concentration.

BACKGROUND ART

Conventionally, there have been some proposals of oral compositions for removing tooth stain.

For example, the pamphlet of International Publication WO 2007/145287 (Patent Document 1) discloses an oral stain remover containing ultraphosphate. The pH of this oral stain remover is 5 to 6.5 (see paragraph [0024] and [0033] of the document).

Japanese Unexamined Patent Publication No. 2009-126819 (Patent Document 2) discloses a dental whitening agent containing hydrogen peroxide or carbamide peroxide as a radical promoter.

Japanese Unexamined Patent Publication No. 2009-024009 (Patent Document 3) discloses a chewing gum composition for removing stain from dental surface, which includes peroxides and polyphosphates.

Japanese Unexamined Patent Publication (Translation of PCT Application) No. 2006-504776 (Patent Document 4) discloses a composition for removing stain from tooth surface, which includes peroxides and polyphosphates.

Japanese Unexamined Patent Publication No. 2009-51734 (Patent Document 5) discloses a liquid composition for oral cavity containing a salt of polyphosphates, acyl taurine salt and polyethylene glycol, the average molecular weight of which is 600, and having pH 7 to 9.

PRIOR ART PUBLICATION

Patent Document

Patent Document 1: International Publication WO 2007/145287

Patent Document 2: Japanese Unexamined Patent Publication No. 2009-126819

Patent Document 3: Japanese Unexamined Patent Publication No. 2009-024009

Patent Document 4: Japanese Unexamined Patent Publication (Translation of PCT Application) No. 2006-504776

Patent Document 5: Japanese Unexamined Patent Publication No. 2009-51734

SUMMARY OF INVENTION

Problems to be Solved by the Invention

Conventional oral compositions can also remove tooth stain. However, there has been desired to develop an oral composition, which can remove tooth stain more effectively.

The object of the present invention is to provide an oral composition, which can remove tooth stain effectively.

Furthermore, the oral stain remover of Patent Document 1 may damage teeth and gums, because it can remove tooth stain only under acidic conditions. Besides, peroxide also causes great damage to teeth and gums. Therefore, the object of the present invention is to provide an oral composition, which scarcely damages teeth and gums and can be easily applied.

Furthermore, peroxide dissolves calcium phosphate including apatite. Namely, the removal of tooth stain by using peroxide causes dissolution of tooth enamel. Therefore another object of the present invention is to provide an oral composition, which prevents dissolution of tooth enamel.

Means for Solving the Problem

The present invention is on the basis of the findings that tooth stain can be removed effectively by containing peroxide and phosphate polymers (in particular ultraphosphate) or its salt at a predetermined concentration. The present invention is also on the basis of the findings that tooth stain can be removed effectively even in neutral pH condition by containing peroxide and the salt of phosphate polymers at a predetermined concentration.

A first aspect of the present invention relates to an oral composition for removing tooth stain. This oral composition comprises 3.5 to 30% by weight of peroxide and 5 to 20% by weight of phosphate polymers (preferably ultraphosphate). The average chain length of polymerization of the ultraphosphate is preferably 10 to 30.

The oral composition realizes dramatically high removal effect compared to the cases of using peroxide or ultraphosphate individually as substantiated in examples. The use of ultraphosphate also realizes very high removal effect compared to the case of the other phosphate polymers. Furthermore, the oral composition has high biocompatibility and high usability, because it works well under neutral pH condition.

Examples of the peroxide are hydrogen peroxide, carbamide peroxide or calcium peroxide.

The oral composition also works well in a neutral region of pH 6.5 to 8 (or pH 6.9 to 7.5).

Preferably, the oral composition further comprises an infrared heating substance, and is irradiated by infrared during use. An example of the infrared heating substance is charcoal. The oral composition can be heated by irradiation of infrared, visible light including infrared or infrared laser to the charcoal. Examples of the charcoal are bamboo charcoal, eggplant charcoal and activated charcoal. The eggplant charcoal is preferable because it has high biocompatibility and realizes high whitening effect by synergy effect with peroxide and ultraphosphate.

Preferably, the oral composition is used at 37 to 50° C. The oral composition cleans more effectively in this temperature range because of increase of the peroxide activity. 37 to 45° C. is more preferable temperature range not to hurt lips, dental pulp and gums by heating.

Preferably, the oral composition further comprises polyethylene glycol, as substantiated in the examples. An example of the average molecular weight of the polyethylene glycol is 4000 to 10000. Preferably, the concentration of the polyethylene glycol is 0.25 to 2% by weight. The structures mentioned above may be combined appropriately.

Advantageous Effects of the Invention

The present invention can provide an oral composition which can remove tooth stain effectively by containing peroxide and phosphate polymers (ultraphosphate) at a predetermined concentration.

Further, in the present invention, containing phosphate polymers (in particular, the salt of, ultraphosphate) can provide an oral composition, which prevents teeth and gums from damage by peroxide.

In particular, the oral composition of the present invention also works well in neutral pH region. Therefore the oral composition of the present invention scarcely damages organism, and tooth cleaning operation can be easily performed by using the oral composition.

Further, in the present invention, the oral composition containing ultraphosphate prevents dissolution of calcium phosphate by peroxide. Therefore, the oral composition of the present invention effectively prevents dissolution of tooth enamel.

DESCRIPTION OF EMBODIMENTS

The oral composition of the present invention is an oral composition for removing tooth stain. Namely, the oral composition is mainly used in oral cavity to remove tooth stain. However, the oral composition of the present invention can be also used to clean a denture or full denture. An example of the oral composition is stain remover. This oral composition may be included in toothpaste or mouse wash and dental rinse. Further, this oral composition may be liquid or gel form. Furthermore, it may be used in whitening performed by dentists.

This oral composition comprises 3.5 to 30% by weight of peroxide and 5 to 20% by weight of phosphate polymers (preferably ultraphosphate) or its salt.

Examples of the peroxide are hydrogen peroxide, calcium peroxide, carbamide peroxide and calcium peroxide. The concentration of the peroxide is preferably 3.5 to 20% by weight or 3.5 to 15% by weight, more preferably 3.5 to 10% by weight, and may be 5 to 10% by weight. Because the cleaning effect of the oral composition of the present invention becomes higher in these temperature ranges as shown in examples.

The oral composition of the present invention comprises phosphate polymers. An example of the polymers is polyphosphate. Among polyphosphates, ultraphosphate is preferable. Examples of ultraphosphate are disclosed in Patent Document 1. A preferable example of ultraphosphate is ultraphosphate with an average chain length of which is 10 to 30 phosphate residues. Further, the average chain length of ultraphosphate may be 15 to 30, and also may be 15 to 25. In particular, when the average chain length is 15 or more, high whitening effect can be observed by synergy effect with peroxide. The concentration of phosphate polymers is preferably 3.5 to 20% by weight, preferably 3.5 to 15% by weight, more preferably 7.5 to 12.5% by weight, more preferably 3.5 to 10% by weight, and may be also 5 to 10% by weight.

The polyphosphate may be added into the composition as a salt. An example of the salt of polyphosphate is a salt of polyphosphate and alkali metal including sodium polyphosphate and potassium polyphosphate.

This oral composition works well under neutral condition of pH 6.5 to 8 (or pH 6.9 to 7.5).

Preferably, the oral composition further comprises an infrared heating substance, and is irradiated by infrared during use. An example of the infrared heating substance is charcoal. Other examples of the infrared heating substance are titanium oxide, aluminum, gold and silver. Generally, infrared laser or other light for whitening use are widely equipped in dental clinics. Further, infrared laser is less harmful than ultraviolet laser for organism. Irradiation of infrared, visible light including infrared or infrared laser causes heating of the charcoal, and then the oral composition including charcoal itself is heated. Therefore whitening effect of the oral composition is increased. The oral composition of the present invention can be used effectively in dental clinic.

The infrared heating substance means a substance, which generates heat by irradiation of infrared. Examples of the wavelengths of the infrared may be 750 to 2000 nm, 800 to 1500 nm, 800 to 1300 nm and 850 to 1050 nm. The present invention also provides an oral composition, which bleaches tooth by being applied to the target tooth and irradiated by infrared. The intensity of the infrared may be 1 to 50 W, 3 to 20 W and 5 to 10 W. The oral composition of the present invention can also increase its whitening effect by irradiation of infrared even if the oral composition does not contain the infrared heating substance. Namely, the present invention also provides an oral composition, which contains peroxide at a certain concentration and bleaches tooth by being applied to the target tooth and irradiated by infrared.

Preferably, this oral composition is used at 37 to 50° C. 37 to 45° C. is more preferable temperature range not to hurt tooth and gums by heating. The oral composition cleans more effectively in this temperature range because of increase of the peroxide activity.

Preferably, the oral composition further comprises polyethylene glycol, as substantiated in the examples. As shown in Tables 6 and 10, which will be mentioned below, an example of the average molecular weight (number average molecular weight) of the polyethylene glycol is 4000 to 10000. The residual ratio of the stain can be reduced when the average molecular weight is 4000 or more. Preferably, the average molecular weight of the polyethylene glycol is 6000 or more. As shown in Table 6, the residual ratio of the stain can be dramatically reduced when peroxide, polyphosphate and PEG exist, because of high degree of synergy effect.

As shown in Table 7, which will be mentioned below, high concentration of polyethylene glycol (PEG) does not always bring about high cleaning ability. Preferably, the concentration of the polyethylene glycol is 0.25 to 2% by weight. The concentration of the polyethylene glycol may be 0.5 to 1.5% by weight or 0.75 to 1.25% by weight.

As shown in Table 9, which will be mentioned below, when peroxide, polyphosphate and PEG exist, containing 7.5 to 12.5% by weight of ultraphosphate brings about extremely high cleaning ability.

In addition to 3.5 to 30% by weight of peroxide and 5 to 20% by weight of polyphosphate (preferably, ultraphosphate), the oral composition may further comprise other compositions used in general oral composition. For example, the oral composition may comprise glycerin, fragrances, coloring agents, flavoring agents and binders. Paste form oral composition can be produced by kneading and mixing of ingredients. Further, liquid form oral composition may be produced by dissolving to solution including water or saline solution.

Example 1

Production of Tea-Stained Dry Apatite as a Colored Tooth Model 1 to 2 g of hydroxyapatite (Biogel-HTP, Bio-Rad Laboratories, Inc.) was put into a 50 mL tube, and 20 mL of protein solution (1%, IXOS SCP5000, Nitta Gelatin Inc.) was added thereto, and the mixture was left to stand for 10 to 15 minutes, and then the mixture was separated by centrifugation at 3,000×g for 2 minutes to remove a supernatant. Next, after the centrifugation, 20 mL of stain solution (5 g of instant coffee, two tea bags and two green tea bags were put into 110 mL of water, and the mixture was heated by a microwave oven for 2 minutes. Then the mixture was cooled down at room temperature with shaking for 3 hours to one night. Then the mixture was filtered by a 200 mesh filter. The stain liquid was obtained like this.) was mixed with the precipitated apatite, and the mixture was left to stand for 10 to 15 minutes, and then the mixture was separated by centrifugation (2,500 rpm, 2 minutes) to remove a supernatant. Then, after centrifugation, 20 mL of artificial saliva (20 mM HEPES-KOH pH 7.0, 1.5 mM $CaCl_2$ and 0.9 mM $KH_2PO_4$) was added into the precipitated apatite, and the mixture was left to stand for 10 to 15 minutes, and then the mixture was separated by centrifugation (2,500 rpm, 2 minutes). After removal of a supernatant from the mixture, the precipitated apatite was dried.

Whitening Effect Evaluation Test 20 mg of the tea-stained dry apatite is weighed, and 0.3 mL of solution was added thereto, which contains $H_2O_2$ at various concentrations and, as appropriate, various phosphate polymers, NaOH and other substances, and then the mixture was left to stand at a certain temperature for a certain time. Then the apatite was precipitated by centrifugation (3,000×g, 15 seconds), and a supernatant was removed from the mixture, and then the apatite was mixed well with 1 mL of water to wash. Further, subsequent washing procedure was repeated four times. After that, the apatite was suspended in 200 µL of water, and the suspension was poured into a well of a 96 well microtiter plate. The 96 well microtiter plate was scanned from the bottom by a scanner (Epson GT8300). The image was inverted to be negative, and brightness analysis was performed by means of imageJ (free software), and then the residual ratio of stain was calculated.

Improvement of Whitening Effect by Ultraphosphate

Table 1 shows the results relating to improvement of whitening effect of hydrogen peroxide by various phosphate polymers.

TABLE 1

Comparison of enhancement of whitening effect of various phosphate polymers

| $H_2O_2$ concentration (%) | Phosphate polymers | Concentration of phosphate polymers (%) | NaOH concentration (N) | pH | Treatment temperature (° C.) | Treatment time (Min.) | Residual ratio of stain (%) |
|---|---|---|---|---|---|---|---|
| 0 | | 0 | 0 | 7 | 45 | | 100.00 |
| 3.5 | Sodium ultraphosphate | 10 | 0 | 7.0 | 45 | 10 | 23.5 |
| 3.5 | Sodium polyphosphale | 10 | 0 | 7.0 | 45 | 10 | 50.4 |

Table 1 shows the result of comparison of improvement ability of whitening effect of hydrogen peroxide by sodium polyphosphate (average chain length is 80 phosphate residues; manufactured by Regenetiss Inc.) and sodium ultraphosphate (manufactured by MITEJIMA CHEMICAL Co., LTD.). Sodium ultraphosphate has twice or more improvement ability of whitening effect than sodium polyphosphate.

Example 2

Relationship Between Concentration of Ultraphosphate and Improvement of Whitening Effect Comparison of whitening effect of 3.5% hydrogen peroxide by using various concentration of sodium ultraphosphate was performed. In this comparison, pH and temperature are fixed to 7.5 and 42° C., respectively, and whitening effect was compared after 10 minutes, 30 minutes, 1 hour and 3 hours. The results are shown in Table 2.

TABLE 2

Improvement of whitening effect of hydrogen peroxide in accordance with the concentration of various ultraphosphate

| $H_2O_2$ concentration (%) | Ultraphosphate concentration (%) | NaOH concentration (N) | pH | Treatment temperature (° C.) | Treatment time | Residual ratio of stain (%) |
|---|---|---|---|---|---|---|
| 3.5 | 0 | 0 | 7.5 | 42 | 10 | 98.15 |
| 3.5 | 0 | 0 | 7.5 | 42 | 30 | 96.80 |
| 3.5 | 0 | 0 | 7.5 | 42 | 60 | 94.89 |
| 3.5 | 0 | 0 | 7.5 | 42 | 180 | 88.78 |
| 3.5 | 1 | 0 | 7.5 | 42 | 10 | 69.60 |
| 3.5 | 1 | 0 | 7.5 | 42 | 30 | 43.56 |
| 3.5 | 1 | 0 | 7.5 | 42 | 60 | 24.43 |
| 3.5 | 1 | 0 | 7.5 | 42 | 180 | 13.86 |
| 3.5 | 5 | 0 | 7.5 | 42 | 10 | 65.82 |
| 3.5 | 5 | 0 | 7.5 | 42 | 30 | 22.75 |
| 3.5 | 5 | 0 | 7.5 | 42 | 60 | 13.98 |
| 3.5 | 5 | 0 | 7.5 | 42 | 180 | 9.06 |
| 3.5 | 10 | 0 | 7.5 | 42 | 10 | 68.12 |
| 3.5 | 10 | 0 | 7.5 | 42 | 30 | 23.47 |
| 3.5 | 10 | 0 | 7.5 | 42 | 60 | 14.28 |
| 3.5 | 10 | 0 | 7.5 | 42 | 180 | 9.43 |
| 3.5 | 15 | 0 | 7.5 | 42 | 10 | 69.42 |
| 3.5 | 15 | 0 | 7.5 | 42 | 30 | 23.61 |
| 3.5 | 15 | 0 | 7.5 | 42 | 60 | 14.73 |
| 3.5 | 15 | 0 | 7.5 | 42 | 180 | 9.93 |
| 3.5 | 20 | 0 | 7.5 | 42 | 10 | 70.30 |
| 3.5 | 20 | 0 | 7.5 | 42 | 30 | 23.05 |
| 3.5 | 20 | 0 | 7.5 | 42 | 60 | 14.02 |
| 3.5 | 20 | 0 | 7.5 | 42 | 180 | 10.10 |

As shown in Table 2, improvement of whitening effect was observed when the concentration of ultraphosphate is 5 to 10%.

Example 3

Variation of Whitening Effect under Various Concentrations of Hydrogen Peroxide

Evaluation of whitening effect under various concentrations of hydrogen peroxide (3.5 to 10%) was performed under the following conditions. (i) ultraphosphate: 5, 10, 20%, (ii) treatment time: 10, 20, 30 minutes, (iii) treatment temperature: 45° C., (iv) pH 7.0. Further as controls, evaluation of individual whitening effects of hydrogen peroxide under alkaline condition (pH 9.5 to 11.6) and ultraphosphate were also performed as comparison groups, and the results are shown in Table 3.

TABLE 3

Whitening effect under various concentrations of hydrogen peroxide and ultraphosphate and treatment time

| $H_2O_2$ concentration | Phosphate polymers | Concentration of phosphate polymers (%) | NaOH concentration (N) | pH | Temperature (° C.) | Treatment time (Min.) | Residual ratio of stain (%) |
|---|---|---|---|---|---|---|---|
| 0 | — | 0 | 0 | | 45 | 30 | 100% |
| 3.5 | — | 0 | 1 | 11.6 | 45 | 30 | 49.23% |
| 5 | — | 0 | 1 | 10.5 | 45 | 30 | 43.17% |
| 10 | — | 0 | 1 | 10.1 | 45 | 30 | 34.47% |
| 20 | — | 0 | 1 | 9.5 | 45 | 30 | 40.08% |
| 3.5 | Ultra | 5 | — | 7.0 | 45 | 30 | 12.44% |
| 3.5 | Ultra | 10 | — | 7.0 | 45 | 30 | 11.42% |
| 3.5 | Ultra | 20 | — | 7.0 | 45 | 30 | 12.76% |
| 3.5 | Ultra | 5 | — | 7.0 | 45 | 20 | 17.33% |
| 3.5 | Ultra | 10 | — | 7.0 | 45 | 20 | 17.21% |
| 3.5 | Ultra | 20 | — | 7.0 | 45 | 20 | 17.15% |
| 3.5 | Ultra | 5 | — | 7.0 | 45 | 10 | 25.36% |
| 3.5 | Ultra | 10 | — | 7.0 | 45 | 10 | 25.10% |
| 3.5 | Ultra | 20 | — | 7.0 | 45 | 10 | 25.98% |

TABLE 3-continued

Whitening effect under various concentrations of hydrogen peroxide and ultraphosphate and treatment time

| $H_2O_2$ concentration | Phosphate polymers | Concentration of phosphate polymers (%) | NaOH concentration (N) | pH | Temperature (° C.) | Treatment time (Min.) | Residual ratio of stain (%) |
|---|---|---|---|---|---|---|---|
| 5 | Ultra | 5 | — | 7.0 | 45 | 30 | 12.05% |
| 5 | Ultra | 10 | — | 7.0 | 45 | 30 | 10.46% |
| 5 | Ultra | 20 | — | 7.0 | 45 | 30 | 11.48% |
| 5 | Ultra | 5 | — | 7.0 | 45 | 20 | 14.28% |
| 5 | Ultra | 10 | — | 7.0 | 45 | 20 | 13.44% |
| 5 | Ultra | 20 | — | 7.0 | 45 | 20 | 15.43% |
| 5 | Ultra | 5 | — | 7.0 | 45 | 10 | 19.63% |
| 5 | Ultra | 10 | — | 7.0 | 45 | 10 | 19.29% |
| 5 | Ultra | 20 | — | 7.0 | 45 | 10 | 19.65% |
| 10 | Ultra | 5 | — | 7.0 | 45 | 10 | 18.49% |
| 10 | Ultra | 10 | — | 7.0 | 45 | 10 | 15.83% |
| 10 | Ultra | 20 | — | 7.0 | 45 | 10 | 14.09% |
| 0 | Ultra | 5 | — | 6.6 | 45 | 30 | 52.65% |
| 0 | Ultra | 10 | — | 6.3 | 45 | 30 | 56.25% |
| 0 | Ultra | 20 | — | 6.1 | 45 | 30 | 56.86% |
| 0 | Ultra | 5 | — | 6.6 | 45 | 20 | 57.69% |
| 0 | Ultra | 10 | — | 6.3 | 45 | 20 | 60.31% |
| 0 | Ultra | 20 | — | 6.1 | 45 | 20 | 57.05% |
| 0 | Ultra | 5 | — | 6.6 | 45 | 10 | 67.59% |
| 0 | Ultra | 10 | — | 6.3 | 45 | 10 | 68.42% |
| 0 | Ultra | 20 | — | 6.1 | 45 | 10 | 62.05% |

As shown in Table 3, when only ultraphosphate was used, every residual ratio of stain were 50% or more, and the result indicates low whitening effect. The 30 minutes treatment of 20% hydrogen peroxide under alkaline condition only results in 40.08%, residual ratio of stain. In contrast, under conditions where 3.5% hydrogen peroxide mixed with 5 to 20% ultraphosphate, or 5% hydrogen peroxide mixed with 5 to 20% ultraphosphate, 12% or less of residual ratio of stain is observed at pH 7.0. These conditions indicated the highest whitening effect among all comparison groups. In particular, compared to the comparison groups with higher concentration of hydrogen peroxide under alkaline conditions, the higher whitening effect was observed at lower concentration of hydrogen peroxide at neutral pH (pH 7.0). These results indicate that damage of tooth and gum caused by hydrogen peroxide were minimized with ultraphosphate. Further, tooth decay is scarcely caused because maximum whitening effect was obtained in pH range above pH 6.5, in which tooth decay begins.

Example 4

Enhancement of Whitening Effect of Carbamide Peroxide Caused by Ultraphosphate

About whitening effect by using carbamide peroxide, instead of hydrogen peroxide, as a radical generator which has whitening ability, evaluation of combination effect with ultraphosphate is shown in Table 4.

TABLE 4

Improvement of whitening effect by combinations of carbamide peroxide and ultraphosphate

| Carbamide peroxide concentration (%) | Phosphate polymers | Concentration of phosphate polymer (%) | NaOH concentration (N) | pH | Temperature (° C.) | Treatment time (Min.) | Residual ratio of stain (%) |
|---|---|---|---|---|---|---|---|
| 0 | — | 0 | 0 | 7.0 | 45 | 30 | 100% |
| 15 | — | 0 | 0 | 7.0 | 45 | 30 | 89.86% |
| 30 | — | 0 | 0 | 7.1 | 45 | 30 | 64.85% |
| 15 | — | 0 | 1 | 11.4 | 45 | 30 | 27.69% |
| 30 | — | 0 | 1 | 10.9 | 45 | 30 | 19.01% |
| 15 | Ultra | 5 | 0 | 7.0 | 45 | 30 | 19.45% |
| 15 | Ultra | 10 | 0 | 7.0 | 45 | 30 | 18.04% |
| 15 | Ultra | 20 | 0 | 7.4 | 45 | 30 | 18.71% |
| 30 | Ultra | 5 | 0 | 7.0 | 45 | 30 | 14.37% |
| 30 | Ultra | 10 | 0 | 7.4 | 45 | 30 | 14.12% |
| 30 | Ultra | 20 | 0 | 6.8 | 45 | 30 | 12.59% |
| 15 | — | 0 | 0 | 7.0 | 45 | 60 | 87.73% |
| 30 | — | 0 | 0 | 7.1 | 45 | 60 | 60.96% |
| 15 | — | 0 | 1 | 11.4 | 45 | 60 | 30.39% |
| 30 | — | 0 | 1 | 10.9 | 45 | 60 | 20.22% |
| 15 | Ultra | 5 | 0 | 7.0 | 45 | 60 | 14.69% |
| 15 | Ultra | 10 | 0 | 7.0 | 45 | 60 | 13.82% |
| 15 | Ultra | 20 | 0 | 74 | 45 | 60 | 15.25% |
| 30 | Ultra | 5 | 0 | 7.0 | 45 | 60 | 10.01% |

TABLE 4-continued

Improvement of whitening effect by combinations of carbamide peroxide and ultraphosphate

| Carbamide peroxide concentration (%) | Phosphate polymers | Concentration of phosphate polymer (%) | NaOH concentration (N) | pH | Temperature (° C.) | Treatment time (Min.) | Residual ratio of stain (%) |
|---|---|---|---|---|---|---|---|
| 30 | Ultra | 10 | 0 | 7.4 | 45 | 60 | 10.27% |
| 30 | Ultra | 20 | 0 | 6.8 | 45 | 60 | 10.25% |

When using carbamide peroxide only, the highest whitening effect is 19.01% (30% of carbamide peroxide, treatment time 60 minutes) under alkaline condition. In contrast, when the treatment, using 15% carbamide peroxide for 30 minutes, was performed under the combination condition with sodium ultraphosphate, residual ratio of stain is 18 to 19%. Further, the lowest residual ratio of stain was 10.01% (in the presence of 5% of ultraphosphate) when 30% carbamide peroxide was used for 60 minutes. These results mean that coexistence of carbamide peroxide and ultraphosphate also brings about high whitening effect.

Example 5

Temperature Dependence of Whitening Effect

Whitening effect at 37, 42 and 45° C. was compared to evaluate the temperature dependence of whitening effect, and the results are shown in Table 5.

TABLE 5

Effect of temperature on enhancement of whitening effect of ultraphosphate

| $H_2O_2$ concentration | Phosphate polymers | Concentration of phosphate polymers (%) | NaOH concentration (N) | pH | Treatment temperature (° C.) | Treatment time (Min.) | Residual ratio of stain (%) |
|---|---|---|---|---|---|---|---|
| 3.5 | Ultra | 5 | 0 | 7.5 | 37 | 10 | 69.61 |
| 3.5 | Ultra | 5 | 0 | 7.5 | 42 | 10 | 65.82 |
| 3.5 | Ultra | 5 | 0 | 7.5 | 45 | 10 | 25.36 |
| 3.5 | Ultra | 10 | 0 | 7.5 | 37 | 10 | 69.91 |
| 3.5 | Ultra | 10 | 0 | 7.5 | 42 | 10 | 68.12 |
| 3.5 | Ultra | 10 | 0 | 7 | 45 | 10 | 25.10 |
| 5 | Ultra | 5 | 0 | 7.5 | 37 | 10 | 53.41 |
| 5 | Ultra | 5 | 0 | 7 | 45 | 10 | 19.63 |
| 5 | Ultra | 10 | 0 | 7.5 | 37 | 10 | 57.34 |
| 5 | Ultra | 10 | 0 | 7 | 45 | 10 | 19.20 |

Table 5 suggested that, when the concentration of hydrogen peroxide is 3.5%, higher temperature brings higher enhancement of whitening effect under both concentration conditions of ultraphosphate (5% and 10%), and the effect was dramatically enhanced at 45° C. Further when the concentration of hydrogen peroxide is 5%, higher effect was obtained at 45° C. than the effect at 37° C. These results suggest that the oral composition of the present invention is preferably used at 42° C. or higher.

Example 6

Effect of Polyethylene Glycol on Whitening (1), Comparison of Whitening Effect Among Polyethylene Glycol Having Different Molecular Weight Whitening effect is evaluated under conditions where various polyethylene glycols, which have different molecular weight (200, 1000, 4000, 6000 and 20000), were added to a mixture of hydrogen peroxide and ultraphosphate so as to have a final concentration of 1%. Other conditions are as follows. (i) ultraphosphate: 10%, (ii) hydrogen peroxide: 0 or 5%, (iii) treatment time: 10 minutes, (iv) treatment temperature: 45° C., and (v) pH 7.0. Further, evaluations of whitening effect of ultraphosphate alone and whitening effect under the condition where ultraphosphate was combined only with hydrogen peroxide were also performed as comparison groups, and the results are shown in Table 6.

TABLE 6

Comparison of enhancement of whitening effect when various polyethylene glycols (PEG), which have different molecular weight, were added to a mixture of hydrogen peroxide and ultraphosphate

| $H_2O_2$ concentration (%) | Ultraphosphate concentration (%) | PEG concentration (%) | Molecular weight of PEG | pH | Treatment temperature (° C.) | Treatment time (%) | Residual ratio of stain |
|---|---|---|---|---|---|---|---|
| 0 | 10 | 0 | — | 7 | 45 | 10 | 93.50 |
| 0 | 10 | 1 | 200 | 7 | 45 | 10 | 92.51 |
| 0 | 10 | 1 | 1000 | 7 | 45 | 10 | 85.96 |
| 0 | 10 | 1 | 4000 | 7 | 45 | 10 | 68.93 |
| 0 | 10 | 1 | 6000 | 7 | 45 | 10 | 68.16 |
| 5 | 10 | 0 | — | 7 | 45 | 10 | 24.49 |
| 5 | 10 | 1 | 200 | 7 | 45 | 10 | 23.94 |
| 5 | 10 | 1 | 1000 | 7 | 45 | 10 | 21.45 |
| 5 | 10 | 1 | 4000 | 7 | 45 | 10 | 19.04 |
| 5 | 10 | 1 | 6000 | 7 | 45 | 10 | 18.59 |

As shown in Table 6, when ultraphosphate was only contained or when polyethylene glycol was added to the ultraphosphate, every residual ratio of stain was 50% or higher, namely these results indicated low whitening effect. On the other hand, when ultraphosphate, hydrogen peroxide and polyethylene glycol were mixed, every residual ratio of stain was less than 25%, namely, about four times higher whitening effect than the case in the absence of hydrogen peroxide was observed. Further, regardless of the presence of hydrogen peroxide, when ultraphosphate and polyethylene glycol were used together, there was a tendency that residual ratio of stain become lower according to the increase of molecular weight of polyethylene glycol. From these results, the highest whitening effect was obtained when 10% ultraphosphate, 1% polyethylene glycol which has the molecular weight of 6000 and 5% hydrogen peroxide were combined, under neutral pH condition at 45° C.

Example 7

Effect of Polyethylene Glycol on Whitening (2), Comparison of Whitening Effect Among Polyethylene Glycol Having Different Molecular Weights and Concentrations Whitening effect is evaluated under conditions where various polyethylene glycols (the molecular weight of 6000), which have different concentrations (0 to 15%), were added to a mixture of hydrogen peroxide and ultraphosphate, and the result is shown in Table 7. Other conditions are as follows. (i) ultraphosphate: 10%, (ii) hydrogen peroxide: 5%, (iii) treatment time: 10 minutes, (iv) treatment temperature: 42° C., and (v) pH 7.0. Further, under the same conditions, comparison of whitening effect, when various polyethylene glycol, which have different molecular weights, were added so as to have different concentrations (0 to 1%), is shown in Table 8.

TABLE 7

Comparison of enhancement of whitening effect when concentrations of polyethylene glycol having a molecular weight of 6000 was varied

| $H_2O_2$ concentration (%) | Ultraphosphate concentration (%) | PEG concentration (%) | Molecular weight of PEG | pH | Treatment temperature (° C.) | Treatment time (%) | Residual ratio of stain |
|---|---|---|---|---|---|---|---|
| 5 | 10 | 0 | — | 7 | 42 | 10 | 32.69 |
| 5 | 10 | 1 | 6000 | 7 | 42 | 10 | 27.96 |
| 5 | 10 | 3 | 6000 | 7 | 42 | 10 | 28.86 |
| 5 | 10 | 5 | 6000 | 7 | 42 | 10 | 28.63 |
| 5 | 10 | 10 | 6000 | 7 | 42 | 10 | 32.29 |
| 5 | 10 | 15 | 6000 | 7 | 42 | 10 | 28.59 |

TABLE 8

Comparison of enhancement of whitening effect when concentraions and molecular weights of polyethylene glycol (PEG) were varied

| $H_2O_2$ concentration (%) | Ultraphosphate concentration (%) | PEG concentration (%) | Molecular weight of PEG | pH | Treatment temperature (° C.) | Treatment time (%) | Residual ratio of stain |
|---|---|---|---|---|---|---|---|
| 5 | 10 | 0 | — | 7 | 42 | 10 | 30.21 |
| 5 | 10 | 0.25 | 4000 | 7 | 42 | 10 | 29.59 |
| 5 | 10 | 0.5 | 4000 | 7 | 42 | 10 | 30.02 |
| 5 | 10 | 1 | 4000 | 7 | 42 | 10 | 29.43 |
| 5 | 10 | 0.25 | 6000 | 7 | 42 | 10 | 31.13 |

TABLE 8-continued

Comparison of enhancement of whitening effect when concentraions and molecular weights of polyethylene glycol (PEG) were varied

| $H_2O_2$ concentration (%) | Ultraphosphate concentration (%) | PEG concentration (%) | Molecular weight of PEG | pH | Treatment temperature (°C.) | Treatment time (%) | Residual ratio of stain |
|---|---|---|---|---|---|---|---|
| 5 | 10 | 0.5 | 6000 | 7 | 42 | 10 | 25.85 |
| 5 | 10 | 1 | 6000 | 7 | 42 | 10 | 25.47 |
| 5 | 10 | 0.25 | 20000 | 7 | 42 | 10 | 26.98 |
| 5 | 10 | 0.5 | 20000 | 7 | 42 | 10 | 25.71 |
| 5 | 10 | 1 | 20000 | 1 | 42 | 10 | 25.27 |

As shown in Table 7, under neutral pH condition at 42° C., residual ratio of stain was 30% or higher when only 10% ultraphosphate and 5% hydrogen peroxide were mixed, and there is a tendency that residual ratio of stain slightly become lower when polyethylene glycol (molecular weight 6000) was further added thereto in range between 1 to 15%. However, no concentration dependence of whitening effect was observed in these cases.

As shown in Table 8, whitening effect was compared under conditions where 1% or less polyethylene glycol was added. Under the condition in the presence of polyethylene glycols having molecular weight of 6000 or 20000 exist, concentration dependence of whitening effect was observed because residual ratio of stain became lower according to increase of concentration. However, when the polyethylene glycol has molecular weight of 4000, similar residual ratio of stain (about 30%), to the ratio in the condition where polyethylene glycol was not added, was observed in every concentration condition, namely no concentration dependence of whitening effect was observed.

As shown in Tables 7 and 8, 0.25 to 1% of polyethylene glycol is enough to enhance whitening effect, and adding more than 1% of polyethylene glycol has no effect on whitening. From these results, it is revealed that noticeable enhancement of whitening effect is observed under neutral pH condition at 42° C., when the polyethylene glycol having 6000 or more of the molecular weight is added so as to have a concentration of 0.25 to 1%

Example 8

Optimization of Mixing Condition of Ultraphosphate, Hydrogen Peroxide and Polyethylene Glycol Whitening effect is evaluated under conditions where polyethylene glycol, which has the molecular weight of 6000, was added to a mixture of hydrogen peroxide and ultraphosphate so as to have a final concentration of 1%, and the result is shown in Table 9. Other conditions are as follows. (i) ultraphosphate: 0 to 20%, (ii) hydrogen peroxide: 5%, (iii) treatment time: 10 minutes, (iv) treatment temperature: 42° C., and (v) pH 7.0. Further, under the same condition, the evaluation of whitening effect was performed under conditions where each polyethylene glycol was added, which has different molecular weight, so as to have a final concentration of 1%, and the concentration of ultraphosphate was fixed at 10%. The result is shown in Table 10.

TABLE 9

Comparison of enhancement of whitening effect in a mixture of hydrogen peroxide, ultraphosphate and PEG when ultraphosphate concentrations were varied

| $H_2O_2$ concentration (%) | Ultraphosphate concentration (%) | PEG concentration (%) | Molecular weight of PEG | PH | Treatment temperature (°C.) | Treatment time (%) | Residual ratio of stain |
|---|---|---|---|---|---|---|---|
| 5 | 0 | 1 | 6000 | 7 | 42 | 10 | 97.61 |
| 5 | 5 | 1 | 6000 | 7 | 42 | 10 | 23.76 |
| 5 | 10 | 1 | 6000 | 7 | 42 | 10 | 22.47 |
| 5 | 20 | 1 | 6000 | 7 | 42 | 10 | 23.19 |

TABLE 10

Comparison of enhancement of whitening effect in a mixture of hydrogen peroxide, ultraphsophate and PEG when molecular weight of PEG was varied

| $H_2O_2$ concentration (%) | Ultraphsopate concentration (%) | PEG concentration (%) | Molecular weight of PEG | pH | Treatment temperature (°C.) | Treatment time (%) | Residual ratio of stain |
|---|---|---|---|---|---|---|---|
| 5 | 10 | 0 | — | 7 | 42 | 10 | 24.32 |
| 5 | 10 | 1 | 200 | 7 | 42 | 10 | 23.77 |
| 5 | 10 | 1 | 1000 | 7 | 42 | 10 | 22.69 |
| 5 | 10 | 1 | 4000 | 7 | 42 | 10 | 22.86 |
| 5 | 10 | 1 | 6000 | 7 | 42 | 10 | 21.78 |
| 5 | 10 | 1 | 20000 | 7 | 42 | 10 | 24.24 |

As shown in Table 9, from the comparison of whitening effect when polyethylene glycol which has the molecular weight of 6000 was added at 1% and the concentration of ultraphosphate was varied from 0 to 20%, it is revealed that every residual ratio of stain under conditions, where ultraphosphate has the concentrations of 5% or more, is 25% or less, and the residual ratios of stain became lowest when the concentration of ultraphosphate is 10%.

On the basis of these results, whitening effect was compared, under conditions where each polyethylene glycol was added, which has different molecular weight, so as to have a concentration of 1%, and the concentration of ultraphosphate was fixed at 10%. From the result of the comparison, it was revealed that enhancement of whitening became more effective in accordance with increase of molecular weight, and the effect was maximized when molecular weight is 6000, as shown in Table 10. From these results, it was revealed that when the treatment temperature was 42° C., addition of polyethylene glycol having the molecular weight of 6000 to a mixture of 5% of hydrogen peroxide and 10% of ultraphosphate so as to have a concentration of 1% brings noticeable high enhancement of whitening effect.

Example 9

Whitening Test Using Detached Teeth (1): 3.5% $H_2O_2$

In order to prepare stain deposited teeth, detached teeth were decolorized by 30% hydrogen peroxide solution for 12 hours or more, and the teeth were soaked in (i) protein solution (for an hour or more), (ii) stain liquid (for 12 hours or more) and (iii) artificial saliva (for an hour or more), in this order. As a protein solution, SPC-5000 (collagen peptide, manufactured by Nitta Gelatin Inc.) was used, and it is dissolved so as to have a concentration of 1 w/v %. To make stain liquid, 5 g of instant coffee, two lipton tea bags and two tea bags of Oi Ocha (registered trademark) were added to 110 mL of distilled water, and the mixture is heated in a microwave oven for about 2 minutes. Then the mixture was cooled down in room temperature, and filtered. The artificial saliva, which is used in this test, had a composition comprising 20 mM HEPES-KOH pH7.0, 1.5 mM $CaCl_2$ and 0.9 mM $KH_2PO_4$. Whitening effect was tested by using the detached teeth stained by the method mentioned above. The following cases were tested, namely, one case that the stained detached tooth was treated with hydrogen peroxide (pH 10) having different concentration (Control Experiment) and the other case that stained detached tooth was treated with hydrogen peroxide and 10% ultraphosphate (pH 7) (Example 1). Then the teeth were incubated at 42° C. for a maximum of 30 minutes.

Figure 1A:
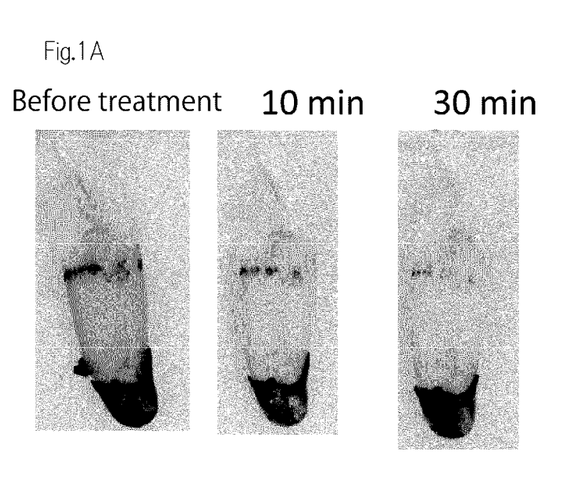
FIG. 1A shows photographs of a tooth, which was treated with 3.5% $H_2O_2$ in alkaline condition (pH 10) at 42° C. for each period of time.
Figure 1B:
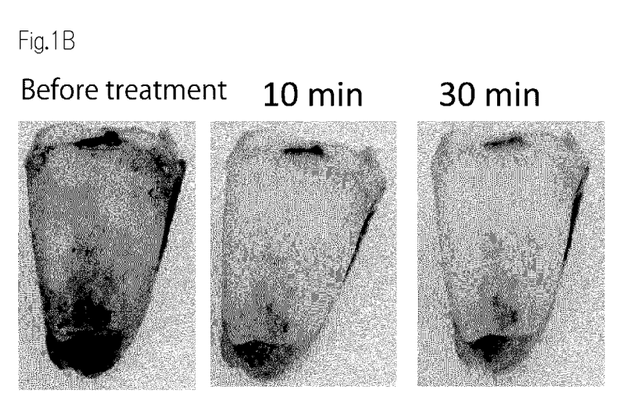
FIG. 1B shows photographs of a tooth, which was treated with 3.5% $H_2O_2$ in alkaline condition (pH 10) at 42° C. for each period of time.
Figure 2A:
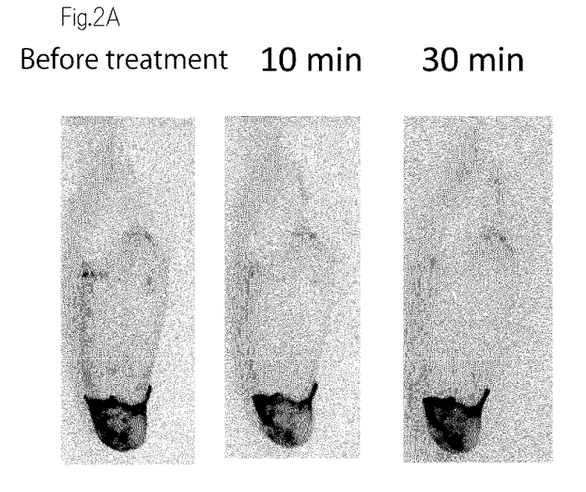
FIG. 2A shows photographs of a tooth, which was treated with 3.5% $H_2O_2$ and 10% sodium ultraphosphate (pH 7) at 42° C. for each period of time.
Figure 2B:
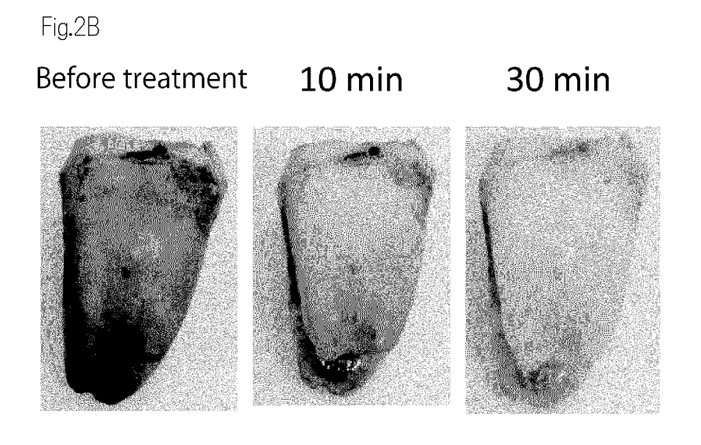
FIG. 2B shows photographs of a tooth, which was treated with 3.5% $H_2O_2$ and 10% sodium ultraphosphate (pH 7) at 42° C. for each period of time.

FIGS. 1A and 1B show photographs of a tooth, which was treated with 3.5% $H_2O_2$ alkaline condition (pH 10) at 42° C. for each period of time (Control Experiment). FIGS. 2A and 2B show photographs of a tooth, which was treated with 3.5% $H_2O_2$ and 10% ultraphosphate (pH 7) at 42° C. for each period of time (Example 1). From comparison between these figures, it is suggested that the combination of 10% ultraphosphate and hydrogen peroxide solution under neutral pH condition brings higher whitening effect than the case of using hydrogen peroxide solution under alkaline condition.

Example 10

Whitening Test Using Detached Teeth (2): 5% $H_2O_2$

The following cases were tested, namely, one case that the stained detached tooth was treated with 5% hydrogen peroxide (pH 10) and the other case that stained detached tooth was treated with 5% hydrogen peroxide and 10% ultraphosphate (pH 7). Then the teeth were incubated at 42° C. for a maximum of 30 minutes.

Figure 3:
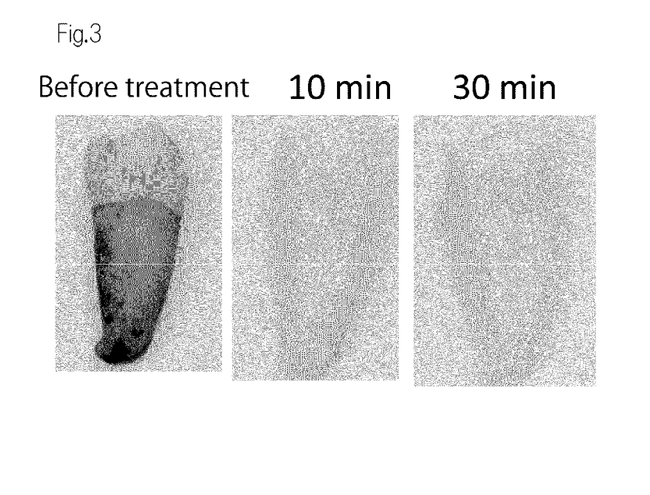
FIG. 3 shows photographs of a tooth, which was treated with 5% $H_2O_2$ (pH 10) at 42° C. for each period of time.
Figure 4:
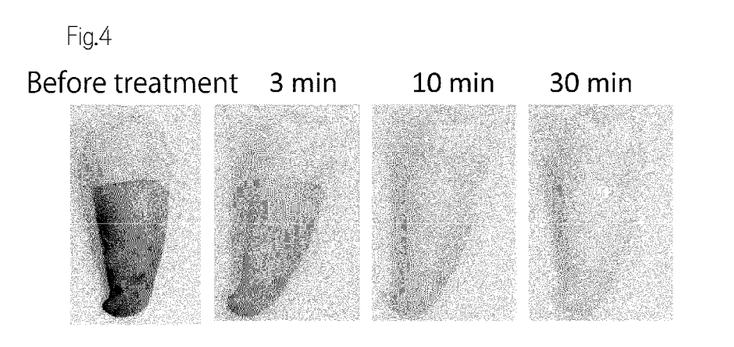
FIG. 4 shows photographs of a tooth, which was treated with 5% $H_2O_2$ and 10% sodium ultraphosphate (pH 7) at 42° C. for each period of time.

FIG. 3 shows photographs of a tooth, which was treated with 5% $H_2O_2$ (pH 10) at 42° C. for each period of time. FIG. 4 shows photographs of a tooth, which was treated with 5% $H_2O_2$ and 10% ultraphosphate (pH 7) at 42° C. for each period of time.

As shown in FIGS. 3 and 4, when whitening test was performed by using 5% hydrogen peroxide, the combination of ultraphosphate and 5% hydrogen peroxide brings higher effect than the case of using 5% hydrogen peroxide alone.

Example 11

Whitening Test Using Detached Teeth (3): 10% $H_2O_2$

One half of the same detached tooth surface was coated with gel containing 10% $H_2O_2$ (pH 10), and the other half of the tooth surface was coated with gel containing 10% $H_2O_2$ (pH 10) with 10% ultraphosphate and prepared so as to have pH 7, and the tooth was incubated at 42° C. for a maximum of 30 minutes. Carboxyvinyl polymer was added to each treatment solution so as to have a final concentration of 0.7% as a thickening agent.

Figure 5:
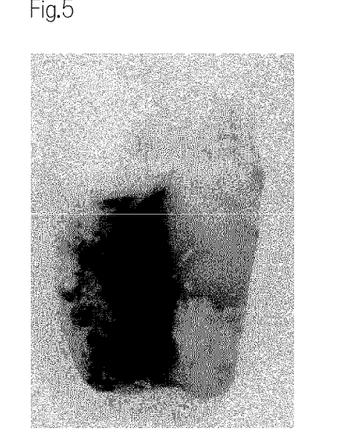
FIG. 5 shows whitening effect on the same detached teeth which was coated with 10% $H_2O_2$ under alkaline condition and polymers including 10% $H_2O_2$ and 10% sodium ultraphosphate under neutral pH condition.

FIG. 5 shows whitening effect on the same detached teeth which was coated with 10% $H_2O_2$ under alkaline condition and polymers including 10% $H_2O_2$ with 10% ultraphosphate under neutral pH condition. As demonstrated on the same tooth in FIG. 5, the case of the polymers including 10% $H_2O_2$ and 10% ultraphosphate under neutral pH condition (the left side) gave higher whitening effect than the case of 10% $H_2O_2$ (the right side).

Example 12

Whitening Test (4) Using Detached Teeth: 20% $H_2O_2$

The following cases were tested, namely, one case that the stained detached tooth was treated with 20% hydrogen peroxide (pH 10) and the other case that stained detached tooth was treated with 20% hydrogen peroxide and 10% ultraphosphate (pH 7). Then the teeth were incubated at 42° C. for a maximum of 30 minutes.

Figure 6A:
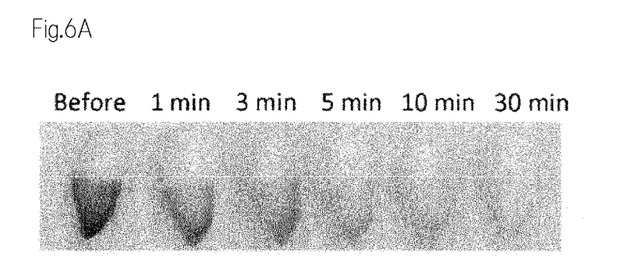
FIG. 6A shows photographs of a tooth, which was treated with 20% $H_2O_2$ (pH 10) at 42° C. for each period of time.
Figure 6B:
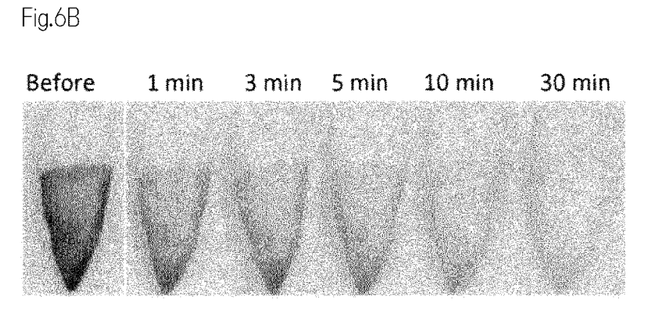
FIG. 6B shows photographs of a tooth, which was treated with 20% $H_2O_2$ (pH 10) at 42° C. for each period of time.
Figure 7A:
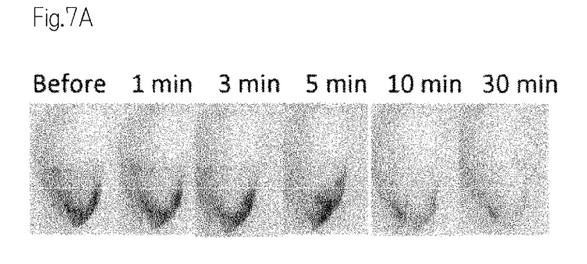
FIG. 7A shows photographs of a tooth, which was treated with 20% $H_2O_2$ and 10% sodium ultraphosphate (pH 7) at 42° C. for each period of time.
Figure 7B:
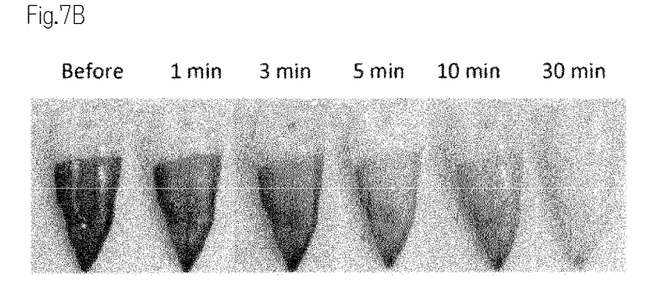
FIG. 7B shows photographs of a tooth, which was treated with 20% $H_2O_2$ and 10% sodium ultraphosphate (pH 7) at 42° C. for each period of time.

FIGS. 6A and 6B show photographs of teeth, which were treated with 20% $H_2O_2$ (pH 10) at 42° C. for each period of time. FIGS. 7A and 7B show photographs of teeth, which were treated with 20% $H_2O_2$ and 10% ultraphosphate (pH 7) at 42° C. for each period of time.

As shown in these figures, when whitening is performed by using 20% hydrogen peroxide, the combination of ultraphosphate and 20% hydrogen peroxide brings lower whitening effect than the case using 20% hydrogen peroxide alone. Namely, when the concentration of hydrogen peroxide is 20% or lower, the oral composition of the present invention seems to be effective. Using 20% hydrogen peroxide alone causes great damage to teeth and gums. On the other hand, the combination of ultraphosphate and 20% hydrogen peroxide gave weaker stimulus than 20% hydrogen peroxide alone.

Example 13

Effect of Infrared Light on Whitening Effect

The oral compositions of above-mentioned examples were applied to teeth, and the applied areas were irradiated by a laser diode for 30 seconds to 5 minutes. Ezlase (registered trademark) manufactured by Waterlase Japan was used as the laser diode. The output wavelength and output intensity of this laser diode were 940 nm and 7 W respectively. As a result, only about one minute irradiation by the laser diode can dramatically enhance whitening effect of tooth. It would appear that whitening effect by peroxide is dramatically enhanced by the energy of the laser diode. Further, the oral composition, to which 1 to 10% by weight of charcoal was added, was applied to teeth, and irradiation was performed in the same way. Then higher whitening effect was confirmed.

INDUSTRIAL APPLICABILITY

The present invention can be utilized in the industry relating to an oral composition.

The invention claimed is:

1. A method for removing tooth stain, the method comprising steps of:
   attaching an oral composition, which comprises 3.5 to 30% by weight of peroxide and 5 to 20% by weight of phosphate polymers or a salt thereof, with tooth; and
   irradiating infrared light to the tooth after attaching the oral composition with the tooth;
   wherein the oral composition further comprises an infrared heating substance, such that the oral composition is heated by irradiation of the infrared light;
   wherein the infrared heating substance is charcoal.

2. A method in accordance with claim 1, wherein the phosphate polymer is ultraphosphate.

3. A method in accordance with claim 2, wherein average chain length of polymerization of the ultraphosphate is 10 to 30.

4. A method in accordance with claim 1, wherein the peroxide is hydrogen peroxide, calcium peroxide or carbamide peroxide.

5. A method in accordance with claim 1, wherein pH of the oral composition is 6.5 to 8.

6. A method in accordance with claim 1, wherein pH of the oral composition is 6.9 to 7.5.

7. A method in accordance with claim 1, wherein the oral composition is used at 37 to 50° C.

8. A method in accordance with claim 1, wherein concentration of the phosphate polymer or its salt is 7.5 to 12.5% by weight.

9. A method in accordance with claim 1, wherein the oral composition further composes polyethylene glycol.

10. A method in accordance with claim 9, wherein average molecular weight of the polyethylene glycol is 4000 to 10000.

11. A method in accordance with claim 9, wherein concentration of the polyethylene glycol is 0.25 to 2% by weight.

* * * * *